United States Patent
Birkhofer et al.

(10) Patent No.: US 6,619,108 B2
(45) Date of Patent: Sep. 16, 2003

(54) METHOD FOR IDENTIFYING THE STATE OF AN NOX STORAGE CATALYST

(75) Inventors: Thomas Birkhofer, Immenstaad (DE); Aleksandar Knezevic, Kirchheim/Teck (DE); Holger Leye, Unterensingen (DE); Ralf Moos, Friedrichshafen (DE); Carsten Plog, Markdorf (DE); Thomas Ried, Uhingen (DE); Dirk Voigtlaender, Korntal-Muenchingen (DE)

(73) Assignee: DaimlerChrysler AG, Stuttgart (DE)

( * ) Notice: Subject to any disclaimer, the term of this patent is extended or adjusted under 35 U.S.C. 154(b) by 0 days.

(21) Appl. No.: 10/026,070

(22) Filed: Dec. 21, 2001

(65) Prior Publication Data

US 2002/0124551 A1 Sep. 12, 2002

(30) Foreign Application Priority Data

Dec. 22, 2000 (DE) ......................... 100 64 499

(51) Int. Cl.[7] ............................................ G01M 15/00
(52) U.S. Cl. ..................................... 73/118.1; 73/118.1
(58) Field of Search ................. 73/1.06, 23.2, 73/23.21, 23.23, 31.03, 31.05, 118.1, 23.31, 23.32

(56) References Cited

U.S. PATENT DOCUMENTS

| | | | |
|---|---|---|---|
| 5,466,350 A | | 11/1995 | Baker et al. |
| 5,950,606 A | * | 9/1999 | Iida et al. .................. 123/672 |
| 6,126,902 A | * | 10/2000 | Kunimoto et al. ............ 422/94 |
| 6,336,354 B1 | * | 1/2002 | Suzuki et al. .............. 73/31.05 |

FOREIGN PATENT DOCUMENTS

| | | |
|---|---|---|
| DE | 43 08 767 | 9/1994 |
| DE | 198 05 928 | 9/1999 |
| DE | 199 16 677 | 1/2001 |
| DE | 199 54 549 | 5/2001 |
| EP | 0 257 842 | 11/1992 |

OTHER PUBLICATIONS

Strehlau W., Leyer J., Lox E.S., Kreuzer T., Hori M., Hoffmann M.: New Developments in Lean NOx Catalysis for Gasoline Fueled Passenger Cars in Europe. SAE Paper 962047 (1996).—Described in specification.

Kato N., Nakagaki K., Ina N.: Thick Film $ZrO_2$ Sensor. SAE Paper 960334 (1996).—Described in specification.

Menil F., Coillard V., Lucat C.: Critical Review of Nitrogen Monoxide Sensors for Exhaust Gases of Lean Burn Engines. Sensors and Actuators B 67 (2000) pp. 1 to 23.—Described in specification.

H. Zhang, et al. "Integration eines smart NOx–Sensors im Abgasstrang für dir Benzindirekteinspritzung" (Integration of a Smart NOx Sensor in the Exhaust Branch for Direct Injection of Gasoline).—Described in specification.

* cited by examiner

Primary Examiner—Kamand Cuneo
Assistant Examiner—Monica D. Harrison
(74) Attorney, Agent, or Firm—Kenyon & Kenyon (57) ABSTRACT

In a method for identifying the state of an NOx storage catalyst which is cyclically loaded with NOx in the exhaust stream of an internal combustion engine and regenerated, two electrical defining quantities, independent of each other, of the electrically complex impedance of the NOx storage catalyst are detected, one of the two electrical quantities being a measure of the degree of loading of the NOx storage catalyst, and from the second electrical quantity the point in time being identifiable for the end of the regeneration process of the NOx storage catalyst.

13 Claims, 11 Drawing Sheets

METHOD FOR IDENTIFYING THE STATE OF AN NOX STORAGE CATALYST

FIELD OF THE INVENTION

The present invention relates to a method for identifying the state of an NOx storage catalyst.

BACKGROUND INFORMATION

The chief emitters of nitrogen oxide (NOx) in the industrial countries are traffic, fossil fuel-fired power stations and industrial plants. Whereas emissions from power stations and from industry are constantly decreasing, the proportion from traffic keeps on becoming more prominent.

NOx emissions from gasoline-driven Otto engines can be drastically reduced by operating at $\lambda=1$ and by cleaning the exhaust gas downstream from the engine using a three-way catalyst. In principle, this possibility does not exist for mixture-regulated Diesel engines which are operated superstoichiometrically. On account of the high oxygen proportion in the exhaust gas, to date no storage catalyst has been realized which can reduce NOx emissions without the addition of reducing agents, such as hydrocarbons or ammonia-forming compounds.

The same is true for lean-operated Otto engines. For that case, there have been vehicles into whose exhaust system branch a storage catalyst is inserted which is operated lean for a certain time ($\lambda>1$) and can store nitrogen oxides during this time. After this "storage phase," in which the storage catalyst is "filled" with the nitrogen oxides to be stored, as a rule, there follows a much shorter desorption phase, also called "regeneration phase," in which the storage catalyst is "emptied." During the desorption phase, the engine is run in rich operation ($\lambda<1$). In reference (1), a storage catalyst is described which is suitable for such requirements. In the literature, the term trap is also used.

In the current concepts for identifying the degree of storage catalyst saturation and the subsequent regulation of fuel/air ratio (air ratio $\lambda$), gas sensors are used which measure the gas to be stored (NOx) downstream from the storage catalyst. Penetration of the gas beyond the storage catalyst indicates in these cases, that the storage catalyst is saturated with the gases to be stored, and that "emptying" (the so-called desorption phase) has to be initiated. Patent documents on NOx sensors (e.g., European Published Patent Application No. 0 257 842, U.S. Pat. No. 5,466,350, German Published Patent Application No. 43 08 767) and other publications (e.g., (2) or (3) as review articles) exist in large numbers. However, such sensors do not detect the degree of storage catalyst saturation, but rather the content of NOx in the exhaust gas. In addition, many of these sensors have stability problems, and besides NOx, they are also cross-sensitive to oxygen and/or water or carbon dioxide. Reference (4) describes a combination sensor which can be built in behind the storage catalyst, which can detect both the air ratio and the NOx content in the exhaust gas, and which is thus suitable for controlling the system of a lean-operated Otto engine. It has to be considered a disadvantage of this method that, only after penetration of the storage catalyst has already occurred can a signal be given to the engine control to "clear up." In addition, the sensor is very expensive. Such a sensor does not show directly the storage state (filling status, degree of filling).

As described in German Published Patent Application No. 199 54 549, however, an operating strategy can be set up which presupposes the presence of a loading sensor, thus achieving more accurate regulation.

German Published Patent Application No. 198 05 928 describes a direct method for identifying the degree of storage catalyst saturation, which identifies the change in the storage catalyst coating (hereafter also designated as storage medium because of its storage properties) on account of a chemical interaction of the nitrogen oxides to be stored with the coating, and which thereby detects the filling state of the storage catalyst.

As described in German Published Patent Application No. 198 05 928, the chemical state of the storage catalyst coating of the monolith, typically made of washcoat, noble metals and storing elements, changes as a function of the degree of saturation, because of the chemical interactions which appear during "storage" and "emptying." With these changes of the coating the physical properties change too, as, for example, the dielectric constant, the electrical conductivity, the refractive index, etc., which can be detected as described in German Published Patent Application No. 198 05 928. German Published Patent Application No. 198 05 928 also describes placing a substitute material having identical or similar properties as the monolith on a suitable transformer, and operating it as storage catalyst state identification sensor.

As described in German Published Patent Application No. 198 05 928, detection of the degree of saturation can be achieved by determination of the complex electrical impedance Z, which also includes the electrical direct current resistance. By complex electrical impedance Z, German Published Patent Application No. 198 05 928 describes the sum of the real part Re(Z) and the imaginary part Im(Z) of the complex impedance Z. The complex electrical impedance Z changes with the measuring frequency applied. The range between 0 Hz (d.c. voltage) and an upper limiting frequency at which the wavelength corresponding to the measuring frequency is substantially smaller than the dimensions of the measuring arrangement, is suitable as the frequency range. As described in German Published Patent Application No. 198 05 928, preferably a suitable measuring frequency is selected, and at this frequency, the complex impedance of the real part and the imaginary part is determined, or a measuring signal is recorded, derived from both or one of these two quantities.

German Published Patent Application No. 199 16 677 describes measuring the dielectric constant of the monolith, which, according to German Published Patent Application No. 199 16 677, differs from $\in_r=8.53$ in the unloaded state (barium carbonate is present, according to German Published Patent Application No. 199 16 677) to $\in_r=4.95$ in the loaded state (barium nitrate).

German Published Patent Application No. 199 16 677 and German Published Patent Application No. 198 05 928 have in common that both use a signal which indicates the loading state. It is true that with such a measuring device one can measure how much nitrogen oxide loading has been applied to the storage catalyst and when the regeneration phase must be initiated, however, it is not possible to decide when the regeneration phase has to be ended. For the operation of a nitrogen oxide-storing exhaust gas cleaning system operated in rich/lean succession, the identification of the optimum point in time for ending the regeneration phase is of the greatest importance. If one ends the regeneration phase too soon, the storage catalyst is not completely emptied, and at the next storage cycle it is possible that nitrogen oxides will no longer be able to be absorbed. That means that nitrogen oxides are emitted. If one ends the regeneration phase too late, breakthrough of the reduction medium occurs, i.e., hydrocarbons are emitted, which should be absolutely avoided.

It is evident from the above, that for a complete determination of the state of a storage catalyst a sensor must deliver two signals which are independent of each other, or which can be attributed to signals independent of each other: one signal indicating the degree of loading and one signal indicating the regeneration state.

SUMMARY

The above and other beneficial objects of the present invention are achieved by providing a method as described herein.

According to the present invention, the complex impedance Z detected by a sensor of the storage catalyst is split into two electrical quantities independent of each other.

The electrical impedance, which may be represented in a two-dimensional coordinate system, is uniquely determined by two defining quantities. Such defining quantities of the complex impedance, that are independent of each other, may include:

ohmic resistance and capacity;

ohmic resistance and amount of the impedance;

amount and real part of the impedance;

amount and phase of the impedance.

Experiments described in more detail below have shown, in particular, that, for detection of the degree of fullness (loading), the ohmic resistance is suitable as measuring quantity at a fixed frequency $f_0$, while the signal of capacity may be used as an indicator for the end of the regeneration phase.

The two defining quantities of the electrical complex impedance, that are independent of each other, may be detected at the same and at different frequencies.

The signals which represent a measure of the nitrogen oxide loading or the regeneration state, as the case may be, are conveyed to the engine electronics. With that, a more accurate regulation may be provided than is the case with the usual model-based regulation using an NOx sensor which only indicates NOx when NOx has already had a breakthrough. In particular, one no longer has to wait until hydrocarbon substances have broken through, in order to end the regeneration phase.

As sensor, one may, for example, use the one described in German Published Patent Application No. 198 059 28 with which the impedance of a substitute material is detected, which is positioned in the exhaust gas stream, together with the storage catalyst. In view of its physical properties, the substitute material is identical or similar to the storage catalyst.

The present invention is not limited to the case of a sensor being used, which is coated with a substitute material. Rather, suitable measuring equipment may be applied on the storage catalyst, e.g., directly on the storage catalyst coating, so that the storage catalyst is diagnosed directly.

Detection of the two defining quantities of the electrical impedance, which are independent of each other, may occur after the storage catalyst or (as seen in the direction of the gas stream) in the rear area of the storage catalyst, e.g., within the last third of the storage catalyst. If storage catalyst is made of several monoliths, a sensor may be installed between two subsequent monoliths.

DETAILED DESCRIPTION

Figure 1:
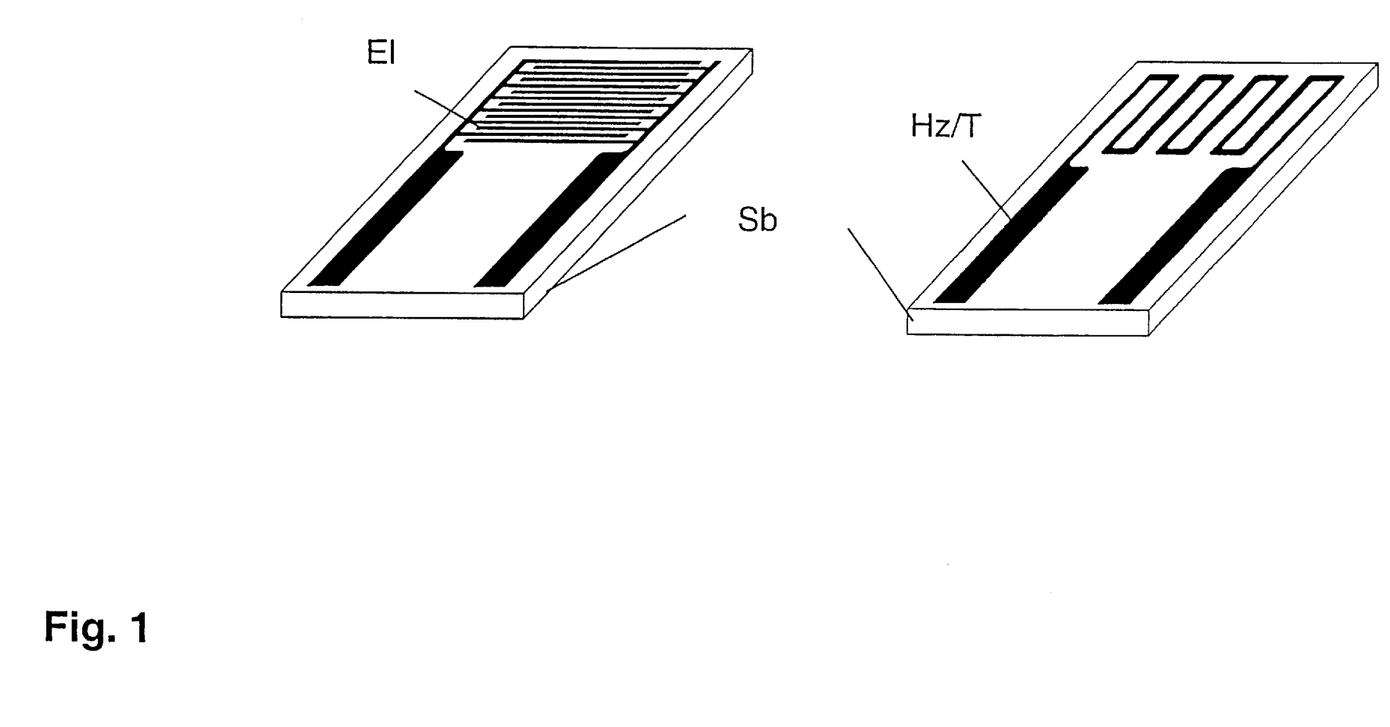
FIG. 1 illustrates the construction of a transmitter made of a substrate, heating and temperature measuring resistor and interdigital capacitor (IDK).

A simple example of a sensor for identifying the state of an NOx catalytic converter may be constructed as illustrated in FIG. 1. A structure Hz/T is applied to the underside of an electrically insulating substrate Sb, made, for example, of aluminum oxide, which permits bringing the sensor to a temperature and/or measuring its temperature. This may typically be done using a zigzag resistance element which may be covered for protective purposes.

Figure 2:
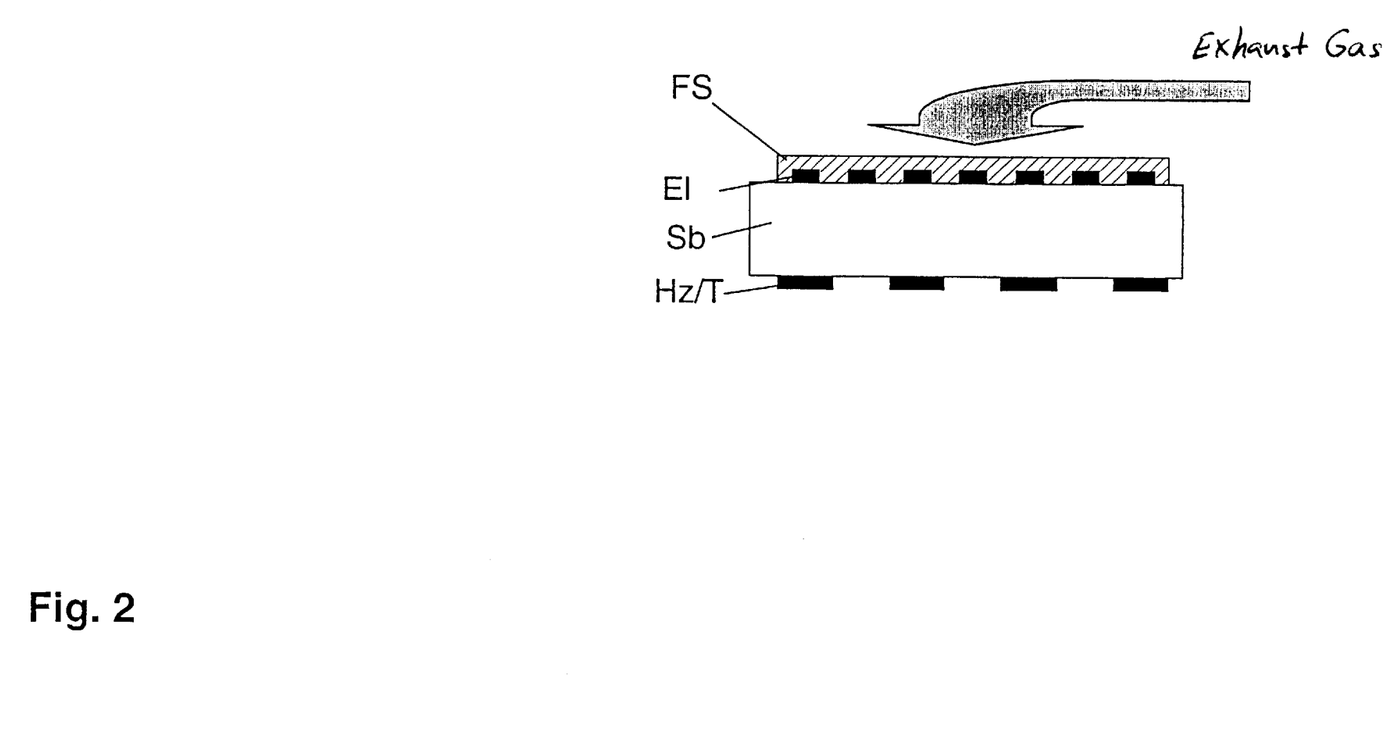
FIG. 2 is a cross-sectional view of the construction illustrated in FIG. 1, in which an identical coating (substitute material) to the catalyst material is applied additionally as function layer.

On the upper side of substrate Sb there is a suitable array El, by which the electrical properties of the catalyst material may be diagnosed. In an example embodiment according to the present invention, this is a so-called interdigital capacitor structure (IDK), in which the "fingers" of two electrodes reach between one another, and thereby form a capacitor. As illustrated in the cross-sectional view of FIG. 2, a layer FS of a substitute material, identical to the catalyst material or one that behaves electrically the same, is deposited on the IDK as a dielectric. Thereby, determination of the complex electrical impedance Z may be achieved, as described, for example, in German Published Patent Application No. 198 05 928. By complex electrical impedance Z, German Published Patent Application No. 198 05 928 describes the sum of the real part Re(Z) and the imaginary part Im(Z) of complex impedance Z. The complex electrical impedance Z changes with the measuring frequency applied. According to German Published Patent Application No. 198 05 928, a suitable measuring frequency may be selected, and at this frequency the complex impedance composed of the real part and the imaginary part is determined, or a measuring signal derived from both or one of these two quantities is introduced.

Figure 3:
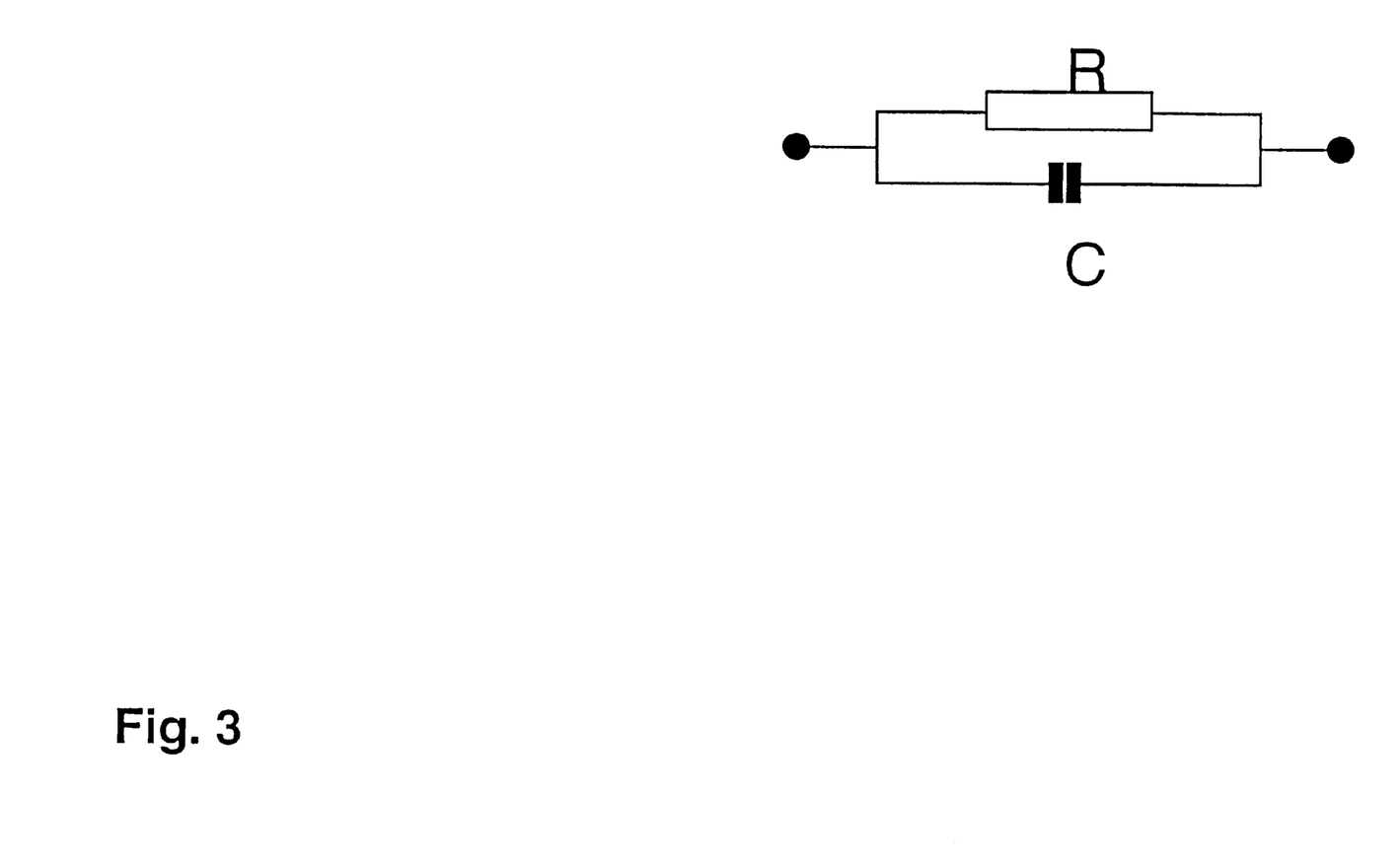
FIG. 3 illustrates a simple electrical analogous circuit made of a parallel connection of a capacitor C and a resistor R.

In contrast to German Published Patent Application No. 198 05 928, according to the present invention, the complex impedance Z is split into two electrical quantities. Experiments, described in greater detail below, indicate that for the detection of the filling state (degree of loading) the ohmic resistance is suitable as measuring variable at a frequency $f_0$, whereas the signal of the capacity may be used as an indicator for the end of the regeneration phase. In this connection, R and C do not necessarily have to be measured at the same frequency $f_0$. The appropriate electrical analogous circuit is illustrated in FIG. 3.

Figure 4:
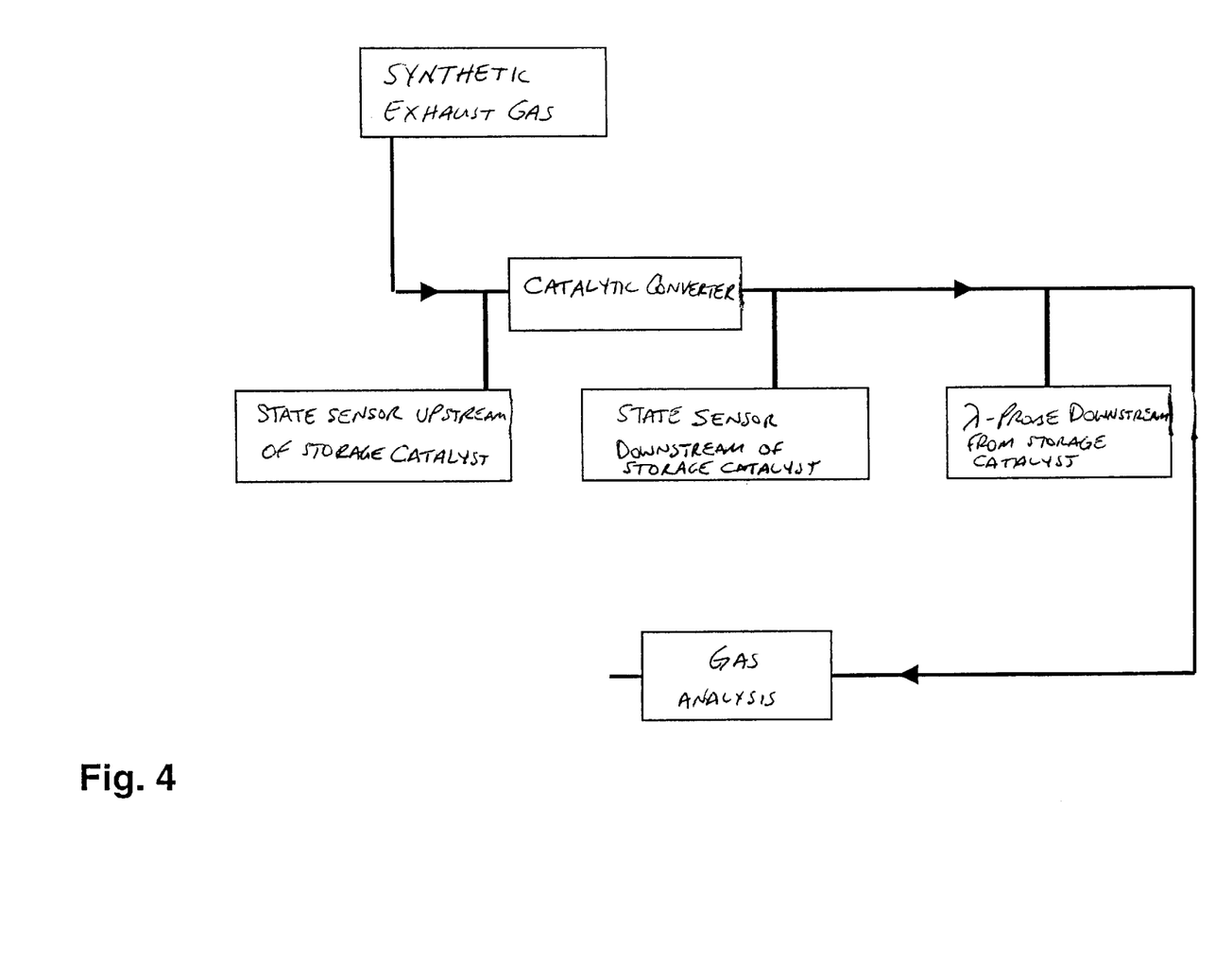
FIG. 4 illustrates the measuring arrangement for the experiments and results introduced in FIG. 5 to FIG. 11.

FIG. 4 illustrates the test arrangement on which the experiments illustrated in FIGS. 5 to 11 was based. A synthetic exhaust gas of known variable composition, which has a composition very close to reality, is conveyed into an NOx storage catalyst. In this arrangement there are two sensors: one sensor upstream of the storage catalyst and one sensor downstream. In order to diagnose the properties of the storage catalyst, an additional gas analysis downstream from the storage catalyst is present, which, within the framework hereof is discussed only with respect to NOx analysis. An additional oxygen-measuring probe, a so-called broadband λ probe, is screwed in downstream from the storage catalyst in order to plot the air ratio λ downstream from the storage catalyst. Storage catalyst and sensor are provided with the same coating as a commercially available NOx storage catalyst. In the experiments, the space velocity was 20,000/h and 40,000/h.

Cyclical rich-lean alternations are performed. The gases applied, and the air ratio resulting therefrom are listed in Table 1.

TABLE 1

| Gas | "Lean" | "Rich" |
|---|---|---|
| NO | 500 ppm or 250 ppm (See description of experiments) | 500 ppm |
| CO | 0.1% | 10% |
| $H_2$ | 333 ppm | 3.33% |
| $CO_2$ | 6% | 12% |
| $O_2$ | 12% | 0% |
| $H_2O$ | 10% | 10% |
| $N_2$ | remainder | remainder |
| λ | 2.1 | 0.75 |

Figure 5:
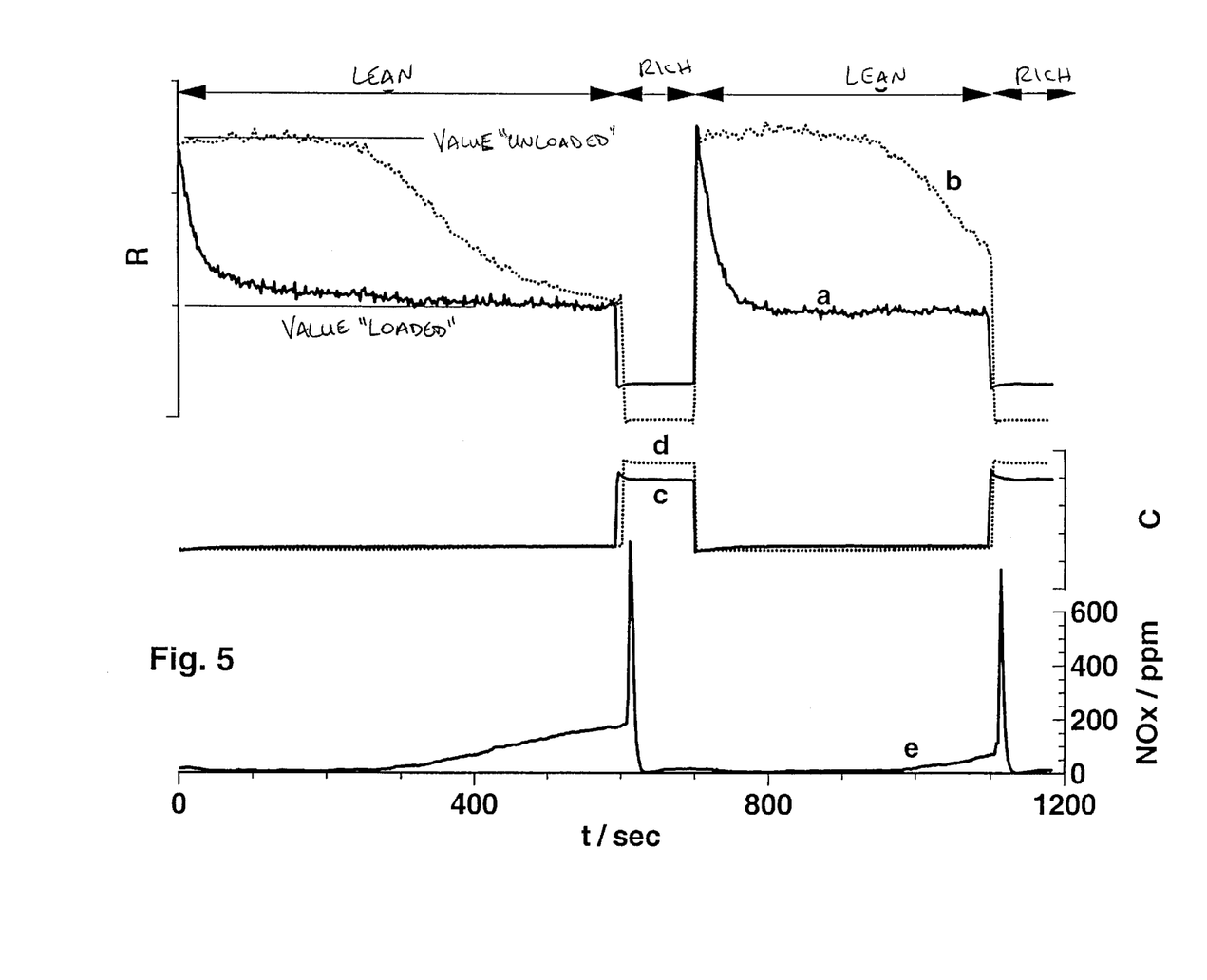
FIG. 5 illustrates a comparison of R and C of a sensor upstream of the storage catalyst and a sensor downstream from the storage catalyst, together with the NOx analysis downstream from the storage catalyst.

A typical experiment is described in conjunction with FIG. 5. The storage catalyst and the two sensors are operated at the same temperature. A measured value was recorded every two seconds. In the lean phase, the process was performed at 250 ppm of NO. The normalized plot of resistor R of the sensor upstream of the storage catalyst is indicated as a solid line (a), the normalized plot of resistor R of the sensor downstream from the storage catalyst as a dotted line (b), the plot of capacity C of the sensor upstream of the storage catalyst as a solid line (c), the plot of capacity C of the sensor downstream from the storage catalyst as a dotted line (d) and the plot of the concentration of the gas downstream from the storage catalyst as a solid line (e). The resistances are found in the upper portion. During the lean phase, the resistance of the sensor downstream from the storage catalyst does not change at first, whereas the sensor upstream of the storage catalyst shows a rapid drop-off, but remains constant after a short time. This value is denoted below as a "loaded" value. Only much later, shortly before the NOx concentration downstream from the storage catalyst rises noticeably, the resistance of the sensor downstream from the storage catalyst also falls off. This is a clear sign that the quantity R indicates the loading state of the NOx catalytic converter, since the loading front first reaches the sensor upstream of the storage catalyst, which in practice represents the first part of the storage catalyst. Only when the entire storage catalyst is loaded, i.e., when the loading front has penetrated all the way to the end, the sensor downstream from the storage catalyst, which represents practically the last part of the storage catalyst, becomes loaded, i.e., its resistance value goes to the value "loaded." At the same time the storage catalyst begins to emit NOx. In a subsequent short, rich phase, storage catalyst and sensor are unloaded (regenerated) again. In the subsequent lean phase, both start again in an unloaded state. The sensor upstream of the storage catalyst (a) becomes loaded again very rapidly, i.e., it very rapidly takes on the "loaded" value. In the case of the sensor downstream from the storage catalyst the loading front arrives only later, i.e., as soon as the storage catalyst begins to break through, it leaves the value "unloaded" so as to tend toward the value "loaded."

It may also be recognized from FIG. 5 that the capacity of the sensors upstream of the storage catalyst and downstream from the storage catalyst does not depend on the loading state, but depends only on whether lean or rich exhaust gas is present, as seen apparently in the rough resolution with respect to time of the experiment illustrated in FIG. 5. This measuring result shows very plainly that R and C are not correlated with each other, at least in the lean operation. The plot of capacity C is discussed below.

Figure 6:
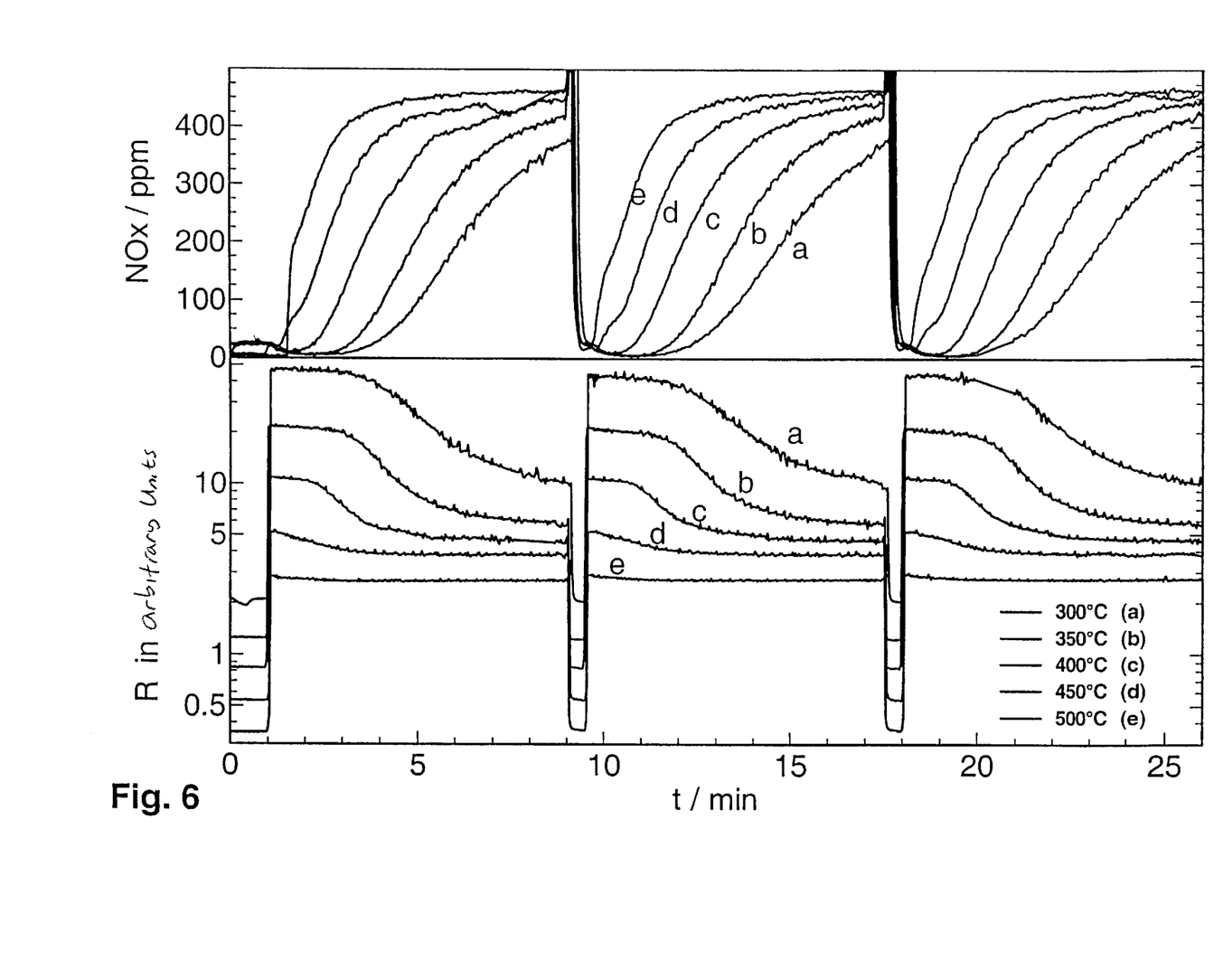
FIG. 6 illustrates the variation with time of resistor R of a sensor downstream from the storage catalyst with temperature as parameter, with storage catalyst and sensor being always brought to the same temperature.

Further proof that R is responsible for the loading state may be recognized with the aid of FIG. 6. There, in turn, resistance R of a sensor downstream from the storage catalyst and the NOx concentration downstream from the storage catalyst are plotted against time for several rich/lean cycles. The NO content in lean operation amounts to 500 ppm. The parameter is the temperature. Storage catalyst and sensor are maintained at the same temperature. One may recognize how, at a low temperature such as 300° C. (curve a), the sensor resistance requires a certain time before going from the unloaded state to the loaded state. Almost at the same time the storage catalyst begins to emit NOx. It is described in the literature that, at increasing temperature, the NOx storability of the storage catalyst decreases, i.e., the storage catalyst breaks through earlier at equal loading. This is verified by curves b to e, which were recorded at increasing temperature. Although the resistance value "loaded" and "unloaded" depend on the temperature, there is always a correlation in time between the beginning of the NOx breakthrough and the falling off of sensor resistance R. The capacity, which is not illustrated in FIG. 6, in this time resolution again illustrates only an almost rectangular characteristic.

Figure 7:
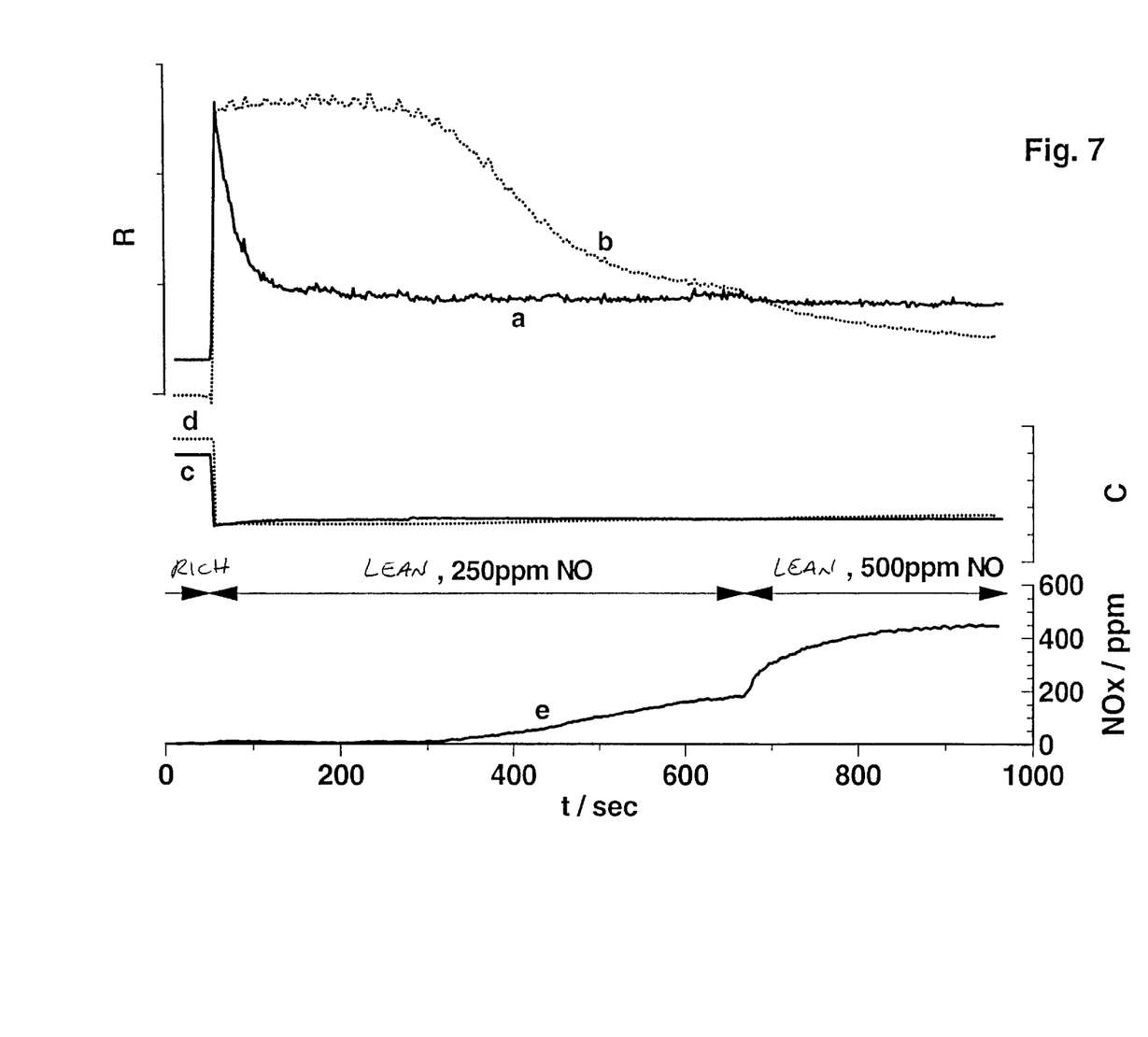
FIG. 7 illustrates the variation of resistor R of a sensor downstream from the storage catalyst, in the lean, loaded state a switch being made from 250 ppm to 500 ppm of NO. The variation with time of the analysis downstream from the storage catalyst is also plotted.

FIG. 7 illustrates a further experiment, which illustrates that the resistance signal is a function of the loading state, and practically not at all of the NOx content of the gas. The storage catalyst is first unloaded in rich operation and then loaded at 250 ppm in the lean exhaust gas. The sensor upstream of the storage catalyst and the sensor downstream from the storage catalyst illustrate the characteristic known from FIG. 5. At time to $t_0 \approx 650$ sec., the storage catalyst has already broken through, but the NOx emission downstream from the storage catalyst has not yet attained the input value of 250 ppm. The sensor upstream of the storage catalyst is practically full already (signal is constant over time) the sensor downstream from the storage catalyst indicates that the storage catalyst is not yet fully loaded (signal is not yet constant, but is approaching the value for loaded). Beginning at $t_0 \approx 650$ sec, 500 ppm NO are applied in lean operation. Since the storage catalyst is practically full, the emission downstream from the storage catalyst takes on the high value at once. If R were a signal dependent on the NO content, and consequently a gas sensor, R would change with the NO content of the gas. However, since R depends on the loading state, it only demonstrates a small change. This change is understandable when one considers that the maximum storable NOx quantity not only depends on the quantity of the storage material available in the storage catalyst, but also on the partial pressure of the NO, which doubles from 250 ppm to 500 ppm NO.

Regarding capacity C, one recognizes again in this resolution in time just a rectangular pattern, independent of the loading state.

The experiments illustrated in FIGS. 5, 6 and 7 illustrate that resistance R indicates the loading of the sensor at the location in the storage catalyst at which it was placed. Capacity C in lean operation is a quantity independent of R, which is not correlated to the degree of loading.

The additional Figures are provided to point out the influence of capacity C. A measuring apparatus was built, which permits measuring capacity C in very quick resolution in time. Every 20 msec., a measured value was sampled and recorded. The system is operated at such a high measuring frequency that the ohmic current is negligible compared to the capacitive current. Then the amount of the complex impedance Z is given by:

$$|Z| \approx (\omega C)^{-1}$$

Figure 8:
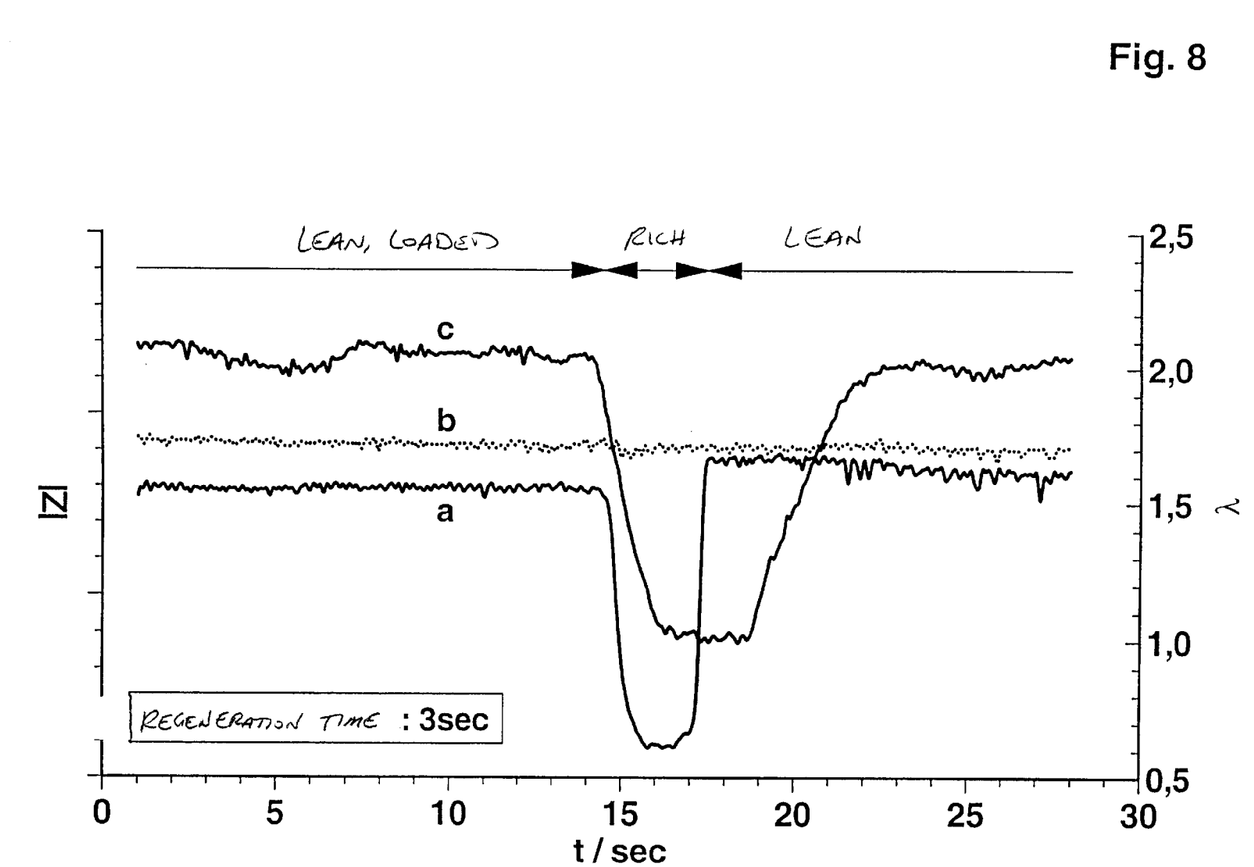
FIG. 8 illustrates the variation with time of the amount of the complex impedance Z of one sensor inserted upstream of the storage catalyst and of one sensor inserted downstream, during the regeneration phase of a storage catalyst, in comparison with an oxygen measuring probe. In this experiment, the regeneration time amounted to three seconds.

The value of the complex impedance of a sensor upstream of the storage catalyst (curve a) and of a sensor downstream from the storage catalyst (curve b) is illustrated in FIG. 8. The storage catalyst was fully loaded in lean operation and was subsequently unloaded (regenerated) beginning at $t_0 \approx 14$ sec. The regeneration process lasted 3 sec. The value of the gas (curve c), measured with the broadband probe downstream from the storage catalyst, is also plotted. It strikes one immediately that the probe changes from $\lambda \approx 2.1$ to $\lambda \approx 1$ at the changeover of the gas from lean to rich. Parallel to that, the sensor upstream of the storage catalyst jumps in the value of the impedance, that is, at this high measuring frequency in the capacity. But the regeneration front has not yet reached the end of the storage catalyst, and thus, the sensor downstream from the storage catalyst. One may see this in curve b, which does not vary, and by the behavior of the $\lambda$ value. For, as soon as the regeneration front reaches the probe, it will jump to the value at which regeneration occurs, i.e., here to $\lambda \approx 0.75$.

Figure 9:
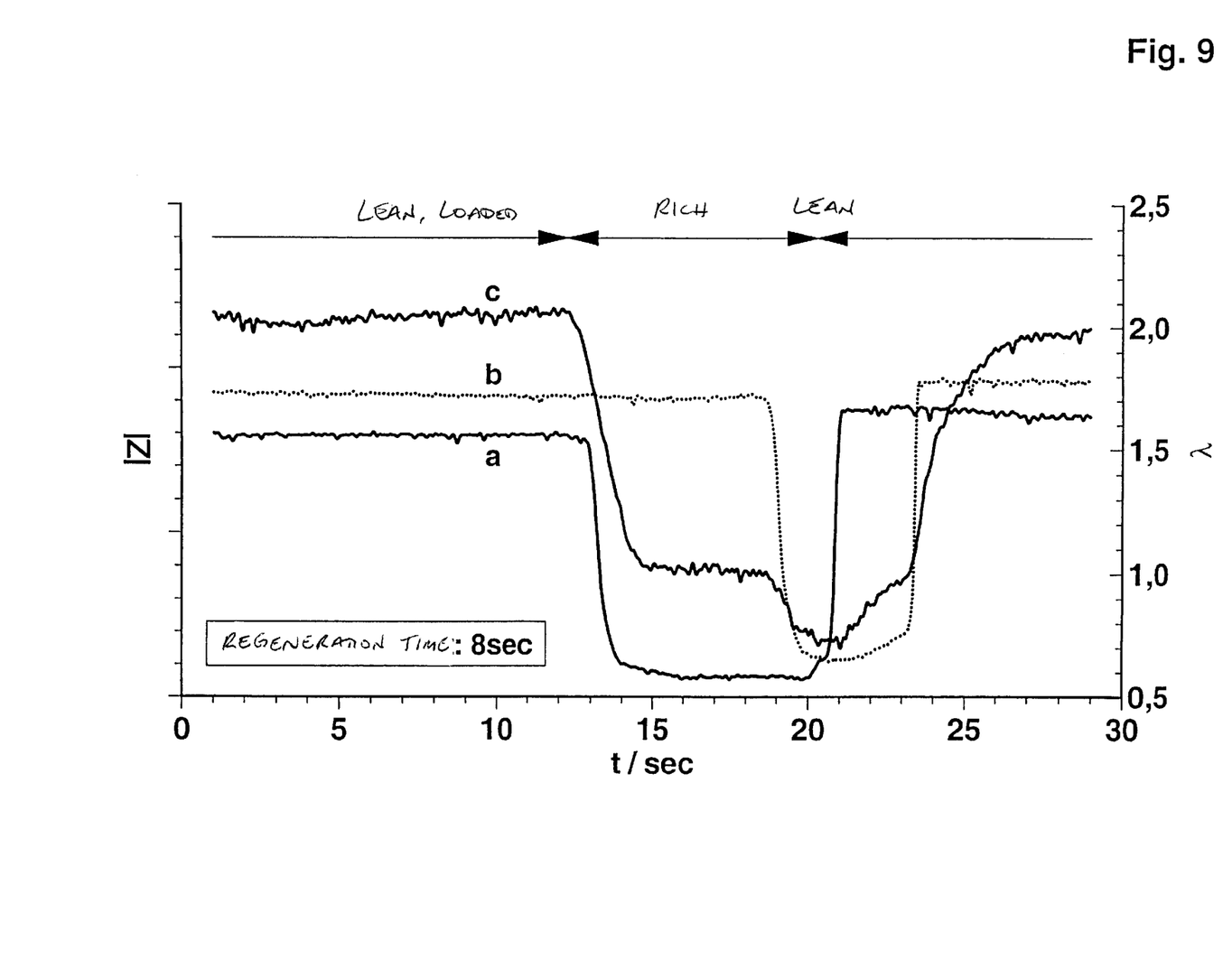
FIG. 9 illustrates the variation with time of the amount of the complex impedance Z of one sensor inserted upstream of the storage catalyst and of one sensor inserted downstream, during the regeneration phase of a storage catalyst, in comparison with an oxygen measuring probe. In this experiment, the regeneration time amounted to eight seconds.

This may be seen in FIG. 9. The storage catalyst has once again been fully loaded in lean operation, and is subsequently regenerated. The regeneration process lasts 8 sec. It is clearly to be seen how the regeneration front reaches the end of the storage catalyst after a certain time. The air ratio $\lambda$ then goes to the $\lambda$ value at which regeneration occurs, i.e., to $\lambda \approx 0.75$. However, the sensor downstream from the storage catalyst jumps at a substantially steeper slope, and thus indicates that the regeneration front has reached the sensor. The characteristic that the $\lambda$ value downstream from the storage catalyst may be used as the signal for ending the regeneration process is described in the literature, see, for example (4), or the literature cited therein. What is new in the example embodiment according to the present invention is, that the measurement of the capacity of the sensor material may in itself tell when the regeneration process ought to be shut off. According to that, a probe downstream from the storage catalyst becomes superfluous.

Figure 10:
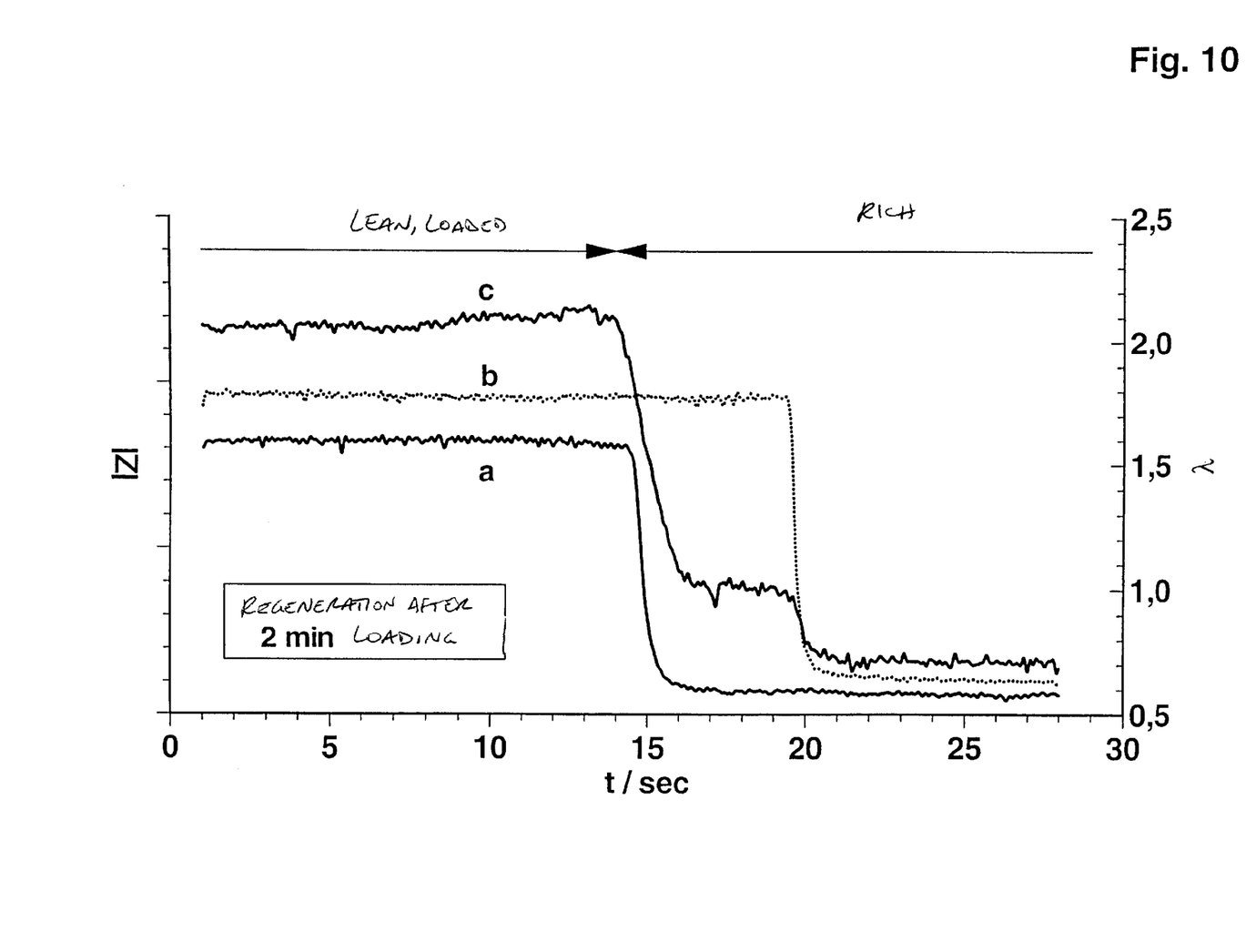
FIG. 10 illustrates the variation with time of the amount of the complex impedance Z of one sensor inserted upstream of the storage catalyst and of one sensor inserted downstream, during the regeneration phase of a storage catalyst, in comparison with an oxygen measuring probe. The previous loading time amounted to two minutes in this experiment.
Figure 11:
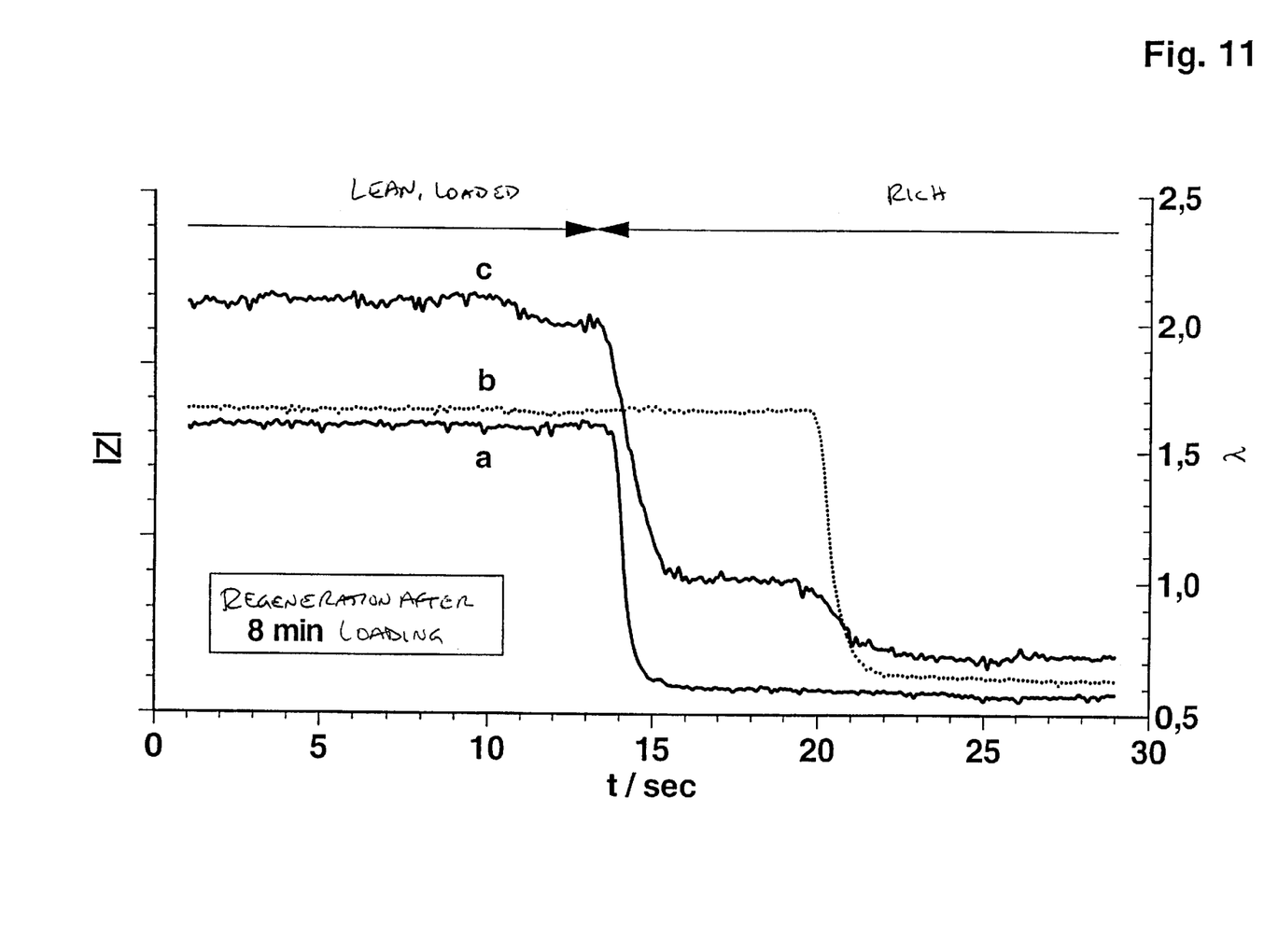
FIG. 11 illustrates the variation with time of the amount of the complex impedance Z of one sensor inserted upstream of the storage catalyst and of one sensor inserted downstream, during the regeneration phase of a storage catalyst, in comparison with an oxygen measuring probe. The previous loading time amounted to eight minutes in this experiment.

FIG. 10 and FIG. 11 confirm the above. As illustrated in FIG. 10, the curve of the quantity |Z| of the complex impedance of a sensor upstream of the storage catalyst (a, solid line) and downstream from the storage catalyst (b, dotted line) is plotted against time. Storage catalyst and sensor are again maintained at the same temperature. The is storage catalyst has been loaded for two minutes. After that, it is regenerated. With the aid of the curve of the sensor signal downstream from the storage catalyst one recognizes at once when the regeneration front reaches the sensor downstream from the storage catalyst. The time difference between the changeover from lean to rich and the jump of the sensor signal downstream from the storage catalyst yields the time necessary for regeneration. As illustrated in FIG. 10, this amounts to approximately 4.8 sec. The same experiment is illustrated in FIG. 11, with the difference that the storage catalyst has been previously loaded for 8 minutes. The time required for regeneration may be determined to be 6.4 sec. It seems evident at once that, with a longer loading time, the storage catalyst requires a longer time for regeneration. This is only not the case, if it was completely full during both loading processes.

These experiments illustrated in FIGS. 8 to 11 illustrate that the jump in capacity, illustrated in FIG. 5, goes along with the regeneration front reaching the sensor, and not with the alternation in the gas from lean to rich.

This being the case, the following operating strategy for the sensor becomes especially available:

A sensor is placed downstream from the storage catalyst or between two monoliths of a nitrogen oxide-storing storage catalyst. It is maintained at the same temperature as the storage catalyst. Two electrical defining quantities, independent of each other, of the impedance Z are measured, or quantities which may be attributed to such signals, that are independent of each other, are measured. These may be, for example, R and C, |Z| and Re(Z) or |Z| and $\phi$. One quantity is then a measure of the degree of loading in lean operation, and the other is a measure of the state of regeneration. The measurement of the two electrical quantities may be made at the same frequency or at different frequencies.

The temperature of the sensor function layer may be detected, using a temperature sensor or a storage catalyst temperature model. In a post-connected electronic clearing unit, a temperature correction may be performed.

In another example embodiment of the present invention, the sensor is maintained at a somewhat higher temperature than the exhaust gas. By doing that, a worse loading capacity is feigned. The regulation of the storage catalyst is then always on the safe side, or, since the sensor (e.g., downstream from the storage catalyst) is then loaded faster, a place for installation of the sensor closer to the engine is feigned. Thus, within certain limits, a larger region of the storage catalyst than the location where the sensor is mounted may be monitored by variations in temperature, using a single sensor.

Literature on the related art (1) Strehlau W., Leyer J., Lox E. S., Kreuzer T., Hori M., Hoffmann M.: New Developments in Lean NOx Catalysis for Gasoline Fueled Passenger Cars in Europe. SAE Paper 962047 (1996).
(2) Kato N., Nakagaki K., Ina N.: Thick Film $ZrO_2$ Sensor. SAE Paper 960334 (1996).
(3) Menil F., Coillard V., Lucat C.: Critical Review of Nitrogen Monoxide Sensors for Exhaust Gases of Lean Burn Engines. Sensors and Actuators B 67 (2000) pp. 1 to 23.
(4) Zhang H., Pfleger C., Lemire B.: Integration eines smart NOx-Sensors im Abgasstrang füur die Benzindirektein-spritzung. (Integration of a Smart NOx Sensor in the Exhaust Branch for Direct Injection of Gasoline).

What is claimed is:

1. A method for identifying a state of an NOx storage catalyst cyclically loaded with NOx and regenerated in an exhaust gas stream of an internal combustion engine, comprising the step of:

detecting two mutually independent electrical defining quantities of a complex electrical impedance of the NOx storage catalyst, a first one of the two quantities being a measure of a degree of loading of the NOx storage catalyst, a point in time for an end of the regeneration of the NOx storage catalyst identifiable from a second one of the two quantities.

2. The method according to claim 1, wherein the two quantities include ohmic resistance and capacity.

3. The method according to claim 1, wherein the two quantities include an amount and a real part of the complex electrical impedance.

4. The method according to claim 1, wherein the two quantities include an ohmic resistance and an amount of the complex electrical impedance.

5. The method according to claim 1, wherein the two quantities include an amount and a phase of the complex electrical impedance.

6. The method according to claim 1, wherein the two quantities are detected in the detecting step at one of equal and different frequencies.

7. The method according to claim 1, wherein the two quantities are detected in the detecting step in a rear region of the NOx storage catalyst in a direction of the exhaust gas stream.

8. The method according to claim 7, wherein the two quantities are detected in the detecting step in a last one-third of the NOx storage catalyst.

9. The method according to claim 1, wherein the two quantities are detected in the detecting step on a substitute material arranged in the exhaust gas stream with the NOx storage catalyst, the substitute material having one of identical and similar physical properties as the NOx storage catalyst.

10. The method according to claim 9, wherein the substitute material is arranged directly behind the NOx storage catalyst.

11. The method according to claim 9, wherein the substitute material is arranged between two subsequent monoliths of the NOx storage catalyst.

12. The method according to claim 9, further comprising the step of maintaining one of the substitute material and the NOx storage catalyst at a higher temperature than a temperature of the exhaust gas at a location that the detecting step is performed.

13. A method for identifying a state of an NOx storage catalyst cyclically loaded with NOx and regenerated in an exhaust gas stream of an internal combustion engine, comprising the step of:

detecting first quantities derived from two mutually independent electrical defining second quantities of a complex electrical impedance of the NOx storage catalyst, a first one of the two second quantities being a measure of a degree of loading of the NOx storage catalyst, a point in time for an end of the regeneration of the NOx storage catalyst identifiable from a second one of the two second quantities.

* * * * *

UNITED STATES PATENT AND TRADEMARK OFFICE
CERTIFICATE OF CORRECTION

PATENT NO. : 6,619,108 B2
DATED : September 16, 2003
INVENTOR(S) : Birkhofer et al.

It is certified that error appears in the above-identified patent and that said Letters Patent is hereby corrected as shown below:

Column 2,
Line 28, change "Z." to -- Z, --;

Column 5,
Line 8, change "Z." to -- Z, --;

Column 8,
Line 22, after "The" delete "is";

Column 9,
Line 5, after "art" insert -- : --; and
Line 17, change "füur" to -- für --.

Signed and Sealed this

Third Day of August, 2004

JON W. DUDAS
*Acting Director of the United States Patent and Trademark Office*